(12) United States Patent
Hess

(10) Patent No.: US 7,111,535 B2
(45) Date of Patent: Sep. 26, 2006

(54) MICROTOME

(75) Inventor: Hans-Juergen Hess, Leimen (DE)

(73) Assignee: Hess Consult GmbH, Leiman (DE)

( * ) Notice: Subject to any disclaimer, the term of this patent is extended or adjusted under 35 U.S.C. 154(b) by 209 days.

(21) Appl. No.: 10/470,110

(22) PCT Filed: Feb. 7, 2002

(86) PCT No.: PCT/DE02/00438

§ 371 (c)(1),
(2), (4) Date: Apr. 5, 2004

(87) PCT Pub. No.: WO02/065095

PCT Pub. Date: Aug. 22, 2002

(65) Prior Publication Data

US 2004/0149106 A1 Aug. 5, 2004

(30) Foreign Application Priority Data

Feb. 9, 2001 (DE) .............................. 101 06 033

(51) Int. Cl.
*G01N 1/06* (2006.01)
(52) U.S. Cl. ................. 83/57; 83/58; 83/703; 83/915.5
(58) Field of Classification Search .................... 83/57, 83/58, 68, 72, 76.9, 276, 703, 915.5; 318/103, 318/571
See application file for complete search history.

(56) References Cited

U.S. PATENT DOCUMENTS

| 3,496,819 | A | * | 2/1970 | Blum ........................... 83/276 |
| 4,479,402 | A | | 10/1984 | Reichel et al. |
| 4,691,151 | A | * | 9/1987 | Behme et al. .............. 318/571 |
| 5,181,443 | A | * | 1/1993 | Sitte et al. ..................... 83/703 |
| 5,226,335 | A | * | 7/1993 | Sitte et al. ..................... 83/703 |
| 6,568,307 | B1 | * | 5/2003 | Gunther et al. ............ 83/915.5 |
| 6,598,507 | B1 | * | 7/2003 | Gunther et al. .............. 83/76.9 |

FOREIGN PATENT DOCUMENTS

| DE | 81 29 032 | 3/1982 |
| DE | 31 27 266 | 1/1983 |
| DE | 199 11 163 | 7/2000 |
| DE | 199 11 005 | 9/2000 |

* cited by examiner

*Primary Examiner*—Stephen Choi
(74) *Attorney, Agent, or Firm*—Bachman & LaPointe, P.C.

(57) ABSTRACT

A microtome includes a knife holding device for a cutting element (16) and a specimen holding device (12). Associated with the specimen holding device (12) for a cutting movement is a first drive device (18) and associated with the specimen holding device (12) or the knife holding device is a second drive device (38) for a feed movement. A sender (20) is associated with the first drive device (18) and is connected with an electronic control means (26). A first operating element (28) controlling the first drive device (18) has a standard mode, in which the cutting movement of the specimen holding device is controlled by rotation of the first operating element (28), and a second mode, in which a continuous cutting function is activated by pressing the first operating element (28). A second operating element (44) controlling the second drive device (38) also has corresponding rotary and pressing modes.

6 Claims, 1 Drawing Sheet

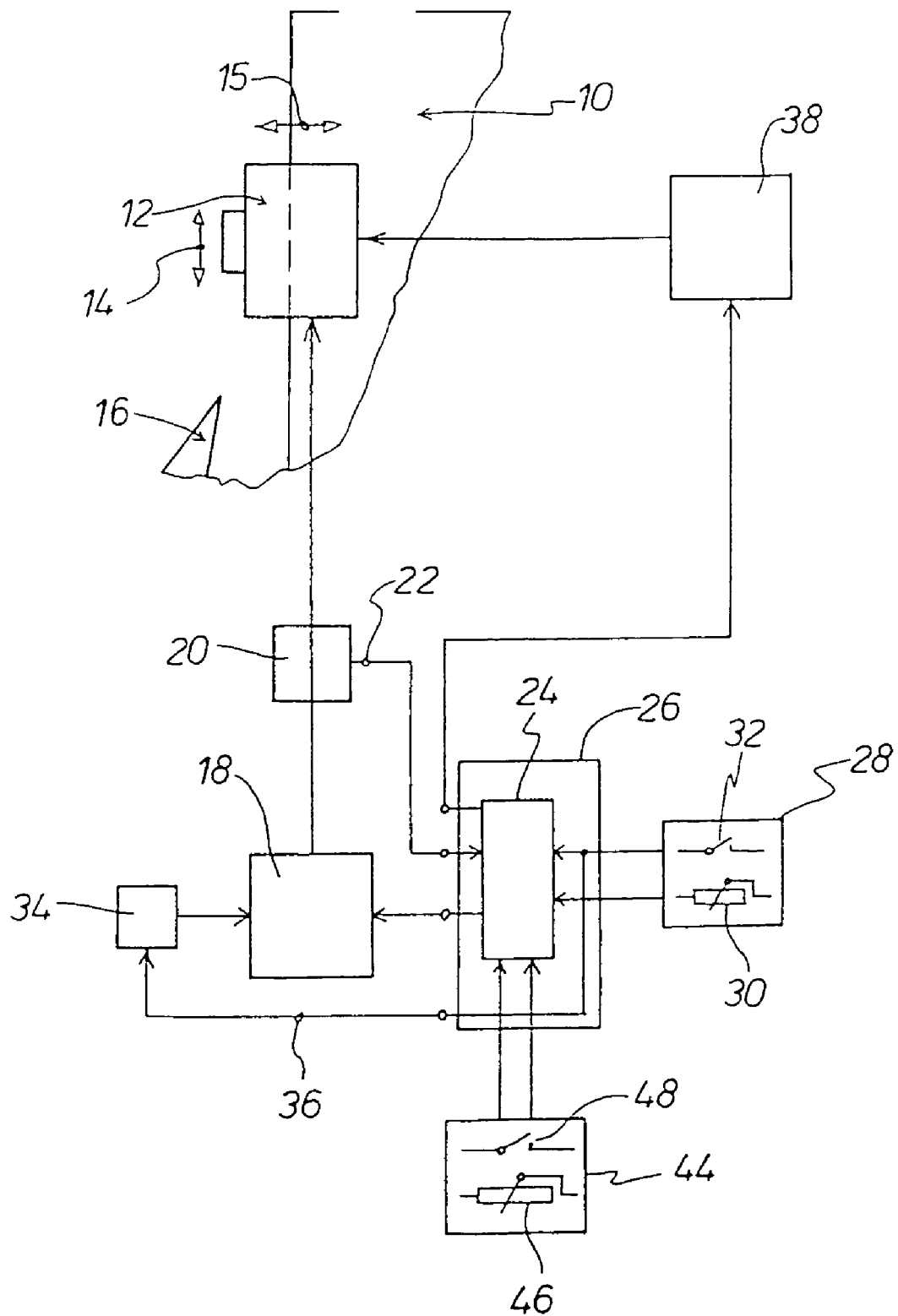

MICROTOME

BACKGROUND OF THE INVENTION

The invention concerns a microtome comprising a knife holding device and a specimen holding device, wherein the specimen holding device has a first drive device for performing a cutting movement and the specimen holding device or the knife holding device has a second drive device for performing a feed movement.

Microtomes of that kind are known per se in various different forms. For example the prospectus 'The MICROM HM 350 S' from MICROM International, 69190 Waldorf, discloses a microtome in which it is possible to eliminate a hand wheel for manual upward and downward movement of the specimen holding device, that is to say for manually performing a cutting movement. The above-mentioned hand wheel is replaced by an operating element which is for example a rotary knob. By way of an incremental generator the rotary knob controls the movements of the specimen holding device, which correspond to the rotary knob. In that known rotational microtome therefore the rotary knob simulates the vertical cutting movement, that is to say the vertical upward and downward movement of the specimen holding device in relation to a base frame of the microtome.

DE 199 11 163 C1 discloses a microtome in which the cutting operation is performed by a relative movement between a cutting knife and a specimen. A drive comprising a drive motor, a control circuit and a hand wheel is provided for producing that relative movement. The hand wheel is connected to an encoder which, upon rotation of the hand wheel, delivers corresponding signals to the control circuit. The drive motor is then suitably actuated by way of that control circuit. The drive is blocked, in the absence of encoder signals. That known microtome therefore has a hand wheel which, upon a rotary movement, delivers signals to the control circuit by way of an encoder. The hand wheel is therefore suitable for carrying out an operating mode corresponding to the standard mode of the microtome according to the invention. There however it is the hand wheel that is actuated and not an operating element; in addition that microtome also has a second control mode in which, by depressing the operating element, the first drive device provided for performing the cutting movement performs a permanent cutting movement of respectively constant speed and amplitude and thus a corresponding continuous cutting function. For that purpose the known microtome has a keyboard, a rotary regulator and switches. The keyboard serves for numerical input, the rotary regulator serves for continuously variable inputs and the switches serve for the input of given switch positions and operating conditions. In that known microtome therefore there are both a hand wheel and also an operating desk with a multiplicity of keys and switches, that is to say operating elements, so that the operating comfort suffers from serious deficiencies. In addition the switches in that microtome do not have a regulating function. The regulating function is first achieved by the additional rotary regulator. In that case therefore, in addition to the hand wheel, the arrangement still requires three different keys or switches, that is to say groups of operating elements, which has a correspondingly detrimental effect on operating comfort. Consequently the design concept of that known microtome corresponds to the well-known configurations having a hand wheel for manual operation, with start/stop keys or buttons for the motor function and a further regulating knob for speed regulation.

DE 199 11 005 A1 discloses a method of controlling a disk microtome in which parameters which are adjustable by motor means are set by way of a control circuit. In that arrangement predetermined reference values for the motor-adjustable parameters are continuously compared to ascertained actual values of the motor-adjustable parameters. Control signals for actuation of the motor-adjustable parameters are formed from the difference between the reference values and the actual values. An external operating desk is connected to the control circuit by way of a control line and a hand wheel, with an associated encoder, is connected to the circuit by way of a second control line. Therefore, that known microtome also has both a hand wheel and also an operating desk so that the level of operating comfort leaves something to be desired in a similar way to the operating comfort of the above-discussed microtome disclosed in DE 199 11 163 C1. A similar consideration also applies in regard to the microtome which is known from DE 31 27 266 A1 and which has an operating and control arrangement connected to a drive and a microprocessor. The speed of rotation of the drive shaft of the drive can be influenced by means of the microprocessor and the operating and control arrangement. An advance selection option for setting the desired cutting region length is provided on an advance transmission of that microtome. Setting is effected by way of a hand wheel. Depending on the respective setting of the hand wheel, a greater or smaller advance movement of the preparation arm is implemented per revolution of the drive shaft. In this known microtome therefore there are both an operating unit and also a hand wheel so that—as in the above—discussed microtomes—the operating comfort still leaves something to be desired.

The object of the invention is to provide a microtome of the kind set forth in the opening part of this specification, with improved operating comfort.

SUMMARY OF THE INVENTION

In accordance with the invention, in a microtome of the kind set forth in the opening part of this specification, that object is attained in that associated with the first drive device is a first operating element which is connected together with an electronic control means of the first drive device, wherein control of the first drive device is effected by way of the electronic control means by means of said first operating element which has two control modes, namely a standard mode in which a cutting movement of the specimen holding device corresponding to the rotary movement of the operating element in respect of speed and amplitude is controlled by corresponding rotation of the operating element, and a second mode in which by laterally pressing the operating element the first drive device performs a permanent cutting movement at a respectively constant speed and amplitude of the specimen holding device and thus a corresponding continuous cutting function.

While the above-mentioned microtome HM 350 S is only suitable for performing the stated standard mode, the microtome according to the invention, by virtue of the operating element being pressed, is also suitable for performing a continuous cutting function, wherein the operating comfort of the microtome is improved by so-called single-knob control.

In the microtome according to the invention the speed of the cutting movement of the specimen holding device advantageously corresponds to the rotary speed of the operating element in its standard mode. In accordance with the invention the specimen holding device can be provided for performing a linearly oscillating cutting movement, that is to say a linearly oscillating up and down movement. Likewise however it is possible for the specimen holding device to perform a cutting movement along a circular path.

The amplitude of the oscillating cutting movement of the specimen holding device corresponds to the amplitude of the rotary movement of the first operating element in its standard mode.

From the point of view of excellent operational reliability and operational safety, it is preferable if, in the microtome according to the invention, the first operating element in its second mode is also suitable for activation of a braking action on the part of the first drive device. The first drive device is preferably formed by a DC motor (direct-current motor).

In accordance with the invention it is also possible for control of the first drive device to be effected by way of an electronic control means by means of a first operating element which has a push button function and a rotary switch function, wherein the first operating element with its push button function controls starting and stopping and with its rotary switching function the speed of the linearly oscillating cutting movement of the specimen holder by way of the first drive device.

In such a configuration of the microtome according to the invention the standard mode, as in the case of a known microtome, can be implemented for example by means of a crank drive which is to be actuated manually, by means of a hand wheel, or the like.

In accordance with the invention, there can be associated with the second drive device a second operating element which is connected together with an electronic control means of the second drive device, wherein control of the second drive device is effected by means of said second operating element which has two control modes, namely a rotary mode and a pressing mode. The electronic control means of the first drive device associated with the specimen holding device and the electronic control means of the second drive device associated with the knife holding device or the specimen holding device respectively can be formed by a common electronic control means.

It is preferred if the/each electronic control means has a CPU which is connected together with the first and/or second drive device and with the associated first and/or second operating element. The first and the second operating elements can each have a rotary rheostat and a push button switch. In the respective rotary mode the corresponding operating element serves to actuate the associated rotary rheostat and in the pressing mode to actuate the respective push button switch. Alternatively for example the first and/or the second operating element can comprise an incremental generator which additionally includes a push button switch for switching over the modes. The two operating elements can be provided on one side of the microtome housing or separately from each other at two different sides of the microtome housing, for example on the right-hand and/or the left-hand side of the microtome housing.

In accordance with the invention, as in the case of conventional rotational microtomes, the coarse advance movement, a trimming advance movement and the fine section thickness can be implemented by a suitable movement of the specimen holding device. Likewise however it is possible for the corresponding advance movement to be produced not by way of the specimen holding device but by way of the knife holding device. In other words, the principle according to the invention of a control procedure by means of a drive device and an associated operating element having two control modes can be applied both to a movement of the specimen holding device and also to a movement of the knife holding device. A corresponding consideration applies in regard to an oscillating movement of the specimen holding device and also a movement of the specimen holding device along a circular path.

In the microtome according to the invention, the second drive device can be provided for stepwise and/or continuous movement of the specimen holding device or the knife holding device in order to produce a corresponding coarse feed movement, a trimming feed movement or a fine section feed movement. The second drive device is preferably formed by a stepping motor.

The horizontally reciprocating movement, that is to say horizontal specimen feed movement, is effected in a microtome according to the invention in the manner of a per se known rotational microtome, for example by means of a screw spindle/spindle nut configuration which is drivable by means of the above-mentioned stepping motor. Control of the stepping motor is effected by way of the associated second operating element and the CPU. Rotation of the second operating element which for example is in the form of a rotary knob, in the one direction of rotation—from a defined zero position—effects a corresponding forward movement of the specimen holding device or the specimen head of the specimen holding device. The speed of that forward movement is correspondingly higher, the further the rotary knob is rotated in the same direction. The speed of the forward movement decreases when the rotary knob is rotated in the opposite direction. When the defined zero position is reached, the horizontal movement of the specimen holding device is stopped. If the rotary knob, that is to say the second operating element, is rotated in the opposite direction of rotation, that affords a corresponding set of movements in the reverse direction of the specimen holding device or the specimen head.

Briefly pressing the second operating element in the zero position causes activation by means of the CPU of a pulse function in which a horizontal advance movement of the specimen holding device is effected by the preselected µm-value which has been respectively selected by way of the section thickness preselection as a trimming feed movement or as a section thickness fine feed movement. The advance movement of the specimen holding device is effected in this mode without a vertical upward and downward movement of the specimen holding device having to be performed.

Such a microtome according to the invention, of the last-mentioned kind, with a first operating element for controlling the vertical upward and downward movement of the specimen holding device and a second operating element for controlling the horizontal reciprocating movement of the specimen holding device, with associated CPU, affords the advantage that for example out of nine operating keys or elements eight operating keys or elements on the operating desk of a conventional microtome can be replaced, namely the operating key for speed preselection of the coarse advance movement, the operating key for the section advance movement forwardly, the operating key for the section advance movement rearwardly, the pulse key for trimming and fine feed movement, the operating key for the start/stop function, the enable/start operating key, the operating key for the braking function, the speed regulator for the cutting movement, and additionally also the conventional mechanical hand wheel, in the usual microtomes.

It is to be mentioned in this connection that medical-technical assistants of both sexes only very reluctantly accept a number of operating keys which trigger or control the corresponding procedural movements, and refer to them as being generally non-ergonomic. Particularly when operating cryostat rotational microtomes the operating keys which are relatively far away from the actuating level frequently give rise to incorrect operations being implemented. In the microtome according to the invention, with one-knob control, that is to say with the at least one operating element or in a particularly advantageous configuration with the two operating elements, such incorrect operations are avoided.

BRIEF DESCRIPTION OF THE DRAWINGS

Further details, advantages and features will be apparent from the description hereinafter of an embodiment, shown in extremely diagrammatic form in the drawing, of a microtome according to the invention in the manner of a rotational microtome wherein—as has been stated above—it will be appreciated that in accordance with the invention the specimen holding device or the knife holding device can perform the corresponding feed movement for coarse cutting, for trimming and for fine cutting, or the invention is not limited to rotational microtomes.

DETAILED DESCRIPTION

The FIGURE is a diagrammatic view showing a portion of a base frame 10 of the microtome. A specimen holding device 12 is arranged on the base frame 10 movably vertically upwardly and downwardly and reciprocatingly horizontally. The microtome is a rotational microtome with a specimen holding device 12 which is suitable for performing a vertical upward and downward movement. That movement is indicated by the double-headed arrow 14. The microtome is also suitable for performing a horizontally reciprocating movement indicated by a double-headed arrow 15. Reference numeral 16 denotes a cutting element of the microtome, of which a portion is diagrammatically indicated. The cutting element 16 is a cutting knife or a knife holder with a cutting blade.

The specimen holding device 12 is connected to an electric motor 18 for implementing the vertical oscillating upward and downward movement indicated by the double-headed arrow 14. The motor 18 is a DC motor. The rotary movement of the electric motor 18 for driving the specimen holding device 12 is detected by a sender 20. The sender is a per se known sensor for detecting a rotary movement, having a signal output 22. Signals are generated at the signal output 22 by means of the sender 20, when the electric motor 18 rotates. The signal output 22 is connected to a CPU 24 of an electronic control means 26. The CPU 24 of the electronic control means 26 also serves for evaluation of the signals of the sender 20, in order to provide for determining the direction of rotation and speed of rotation of the electric motor 18.

The signals of the sender 20 are therefore passed directly to the CPU 24. Besides the CPU, the electronic control means 26 has further modules. At regular time intervals, the corresponding information from the sender 20 is acquired by the CPU 24 and converted into corresponding items of information relating to speed and direction of rotation. Those items of information then serve as reference values for a speed regulator of the electric motor 18. Calculation of the speed reference values takes place in the software of the CPU 24 of the electronic control means 26 so that so-to-speak an electronic transmission is embodied between the electric motor 18 and the specimen holding device 12. The rotary speed of the electric motor 18 can thus be defined as a function of the speed of an operating element 28 which is operatively connected to the CPU 24 of the electronic device 26. The reference value, calculated by means of the CPU 24, for the speed regulator is converted into a control signal of a power stage which generates the electrical energy for the electric motor 18.

The operating element 28 is displaceable between two control modes, namely a per se known standard mode and a second mode. In the first, that is to say standard mode of the operating element 28, a rotary movement of the operating element 28 is converted into a corresponding upward and downward movement of the specimen holding device 12. That applies both in respect of the speed of the upward and downward movement of the specimen holding device 12 in accordance with the rotary speed of the operating element 28 and also in respect of the amplitude of the upward and downward movement of the specimen holding device 12 in accordance with the amplitude of the rotary movement of the operating element 28 in the specified standard mode. The second mode is activated by pressing the operating element 28. In that second mode the electric motor 18 performs a permanent upward and downward movement, that is to say a continuous cutting function of the specimen holding device 12.

For that purpose the operating element 28 may have for example a rotary rheostat 30 and a push button switch 32 which in the FIGURE are only diagrammatically indicated—like the electric motor 18, the sender 20, the CPU 24 and the electronic control means 26 as well as the operating element 28.

The electric motor 18 is connected to a motor brake 34 which is also only diagrammatically indicated by a block. In the second mode the operating element 28 is also suitable for activating the motor brake 34 of the electric motor 18. That is diagrammatically indicated by the angled arrow 36.

In the microtome according to the invention, in particular a rotational microtome, the operating element 28 therefore has a dual function. In the standard mode the upward and downward movement of the specimen holding device 12 is controlled in respect of its speed and amplitude by suitably rotating the operating element 28 for example in the form of a rotary knob, in the forward and back direction. In the second mode which is activated for example by laterally pressing on the rotary knob the electric motor 18 is permanently activated so that the specimen holding device in that second mode performs a permanent upward and downward movement, that is to say a continuous cutting function. In that case the cutting speed of the continuous cutting function can be regulated by rotating the rotary knob in the clockwise direction or in the counter-clockwise direction. The regulating range begins for example upon laterally pressing on the rotary knob at zero and extends as far as a defined maximum speed. When the rotary knob is pressed once again the cutting cycle is appropriately terminated at the upper reversal point of the specimen holding device 12 and the motor brake 34 is activated. By simply rotating the rotary knob 28 without pressing it, the motor brake 34 can be released again and the manual mode is introduced or implemented.

In the microtome according to the invention cutting speed regulation can be effected in two programs, that is to say in a program I and a program II:

With the program I the regulating speed begins at zero by pressing the rotary knob and by virtue of rotation of the rotary knob goes up to a maximum speed and goes back to zero again by rotation in the opposite direction.

With program II the regulating speed begins, by pressing the rotary knob, at a medium cutting speed which can be freely programmed. The regulating speed can thereafter be set to any desired speed by specific rotary movement of the rotary knob. When the rotary knob or operating element 28 is repeatedly pressed in both of the above-mentioned programs the cutting cycle can be stopped at the upper reversal point of the specimen holding device 12 and the motor brake 34 activated.

By suitable programming, stopping of the vertical cutting movement can be effected upon repeated pressing of the operating element 28 at any x-desired point and the motor brake 34 activated.

Therefore, with what is known as one-knob control, by means of the operating element 28, all possible vertical movements of a manual hand wheel drive of the specimen holding device 12 of known microtomes are automated in a logical manner and without physical exertion and strain. The one-knob control according to the invention, in comparison with known motorised microtomes, unites the following functions:

on/off automatic specimen stroke movement;
brake;
up-and-down of the specimen holding device manually; and
speed regulation of the specimen holding device.

The specimen holding device 12 is also connected to an electric motor 38 which can be for example a stepping motor for implementing a horizontally reciprocating movement which is indicated by the double-headed arrow 15.

The electric motor 38 is connected by way of the CPU 24 of the electronic control means 26 to an associated second operating element 44. Like the first operating element 28, the second operating element 44 has two modes, namely a rotary mode and a pressing mode. The rotary mode of the second operating element 44 is indicated by a rotary rheostat 46 and the pressing mode of the second operating element 44 is indicated by the symbol of a push button switch 48. Rotating the second operating element 44 in one direction of rotation—from a defined zero position—provides for corresponding horizontal forward movement of the specimen holding device 12, as already stated above. The speed of that forward movement is proportional to the respective angle of rotation of the second operating element 44, that is to say the speed of the forward movement increases, the more the second operating element 44 is further rotated in the same direction. The speed of the forward movement of the specimen holding device 12 decreases if the second operating element 44 is rotated in the opposite direction of rotation. When the defined zero position of the specimen holding device 12 is reached, the horizontal movement of the specimen holding device 12 is stopped. If the operating element 44 is rotated in the opposite direction of rotation, then the corresponding movements of the specimen holding device 12 take place in opposite relationship to the forward direction, that is to say in the rearward direction. If the second operating element 44 is pressed in the zero position of the specimen holding device 12, a pulse function is activated, in which a horizontal advance movement of the specimen holding device 12 is effected by the respectively set µm-value which has been preselected by means of the section thickness preselection option of the microtome as a trimming feed movement or as a fine section feed movement. In this mode the advance movement of the specimen holding device 12 takes place without vertical movement of the specimen holding device 12 in the direction of the double-headed arrow 14.

The first operating element 28 and the second operating element 44 can be located at one and the same side of the microtome housing or on two mutually different sides of the microtome housing, that is to say for example on sides which are facing away from each other.

Besides the advantages of a considerable cost reduction and very great ease of operability, the microtome according to the invention has the quite considerable advantage of optimum ergonometry so that the known illnesses caused by operation such as carpal tunnel syndrome and repetitive motion diseases are quite substantially reduced or eliminated.

The invention claimed is:

1. A microtome comprising a knife holding device for a cutting element (16) and a specimen holding device (12), wherein the specimen holding device (12) has a first drive device (18) for performing a cutting movement, and the specimen holding device (12) or the knife holding device has a second drive device (38) for performing a feed movement, wherein associated with the first drive device (18) is a first operating element (28) which is connected together with an electronic control means (26) of the first drive device (18), wherein control of the first drive device (18) is effected by way of the electronic control means (26) by means of the first operating element (28), wherein the first operating element (28) has two control modes, namely a standard mode in which a cutting movement of the specimen holding device (12) corresponding to the rotary movement of the operating element (28) is controlled by corresponding rotation of the operating element (28), and a second mode in which by pressing the operating element (28) the first drive device (18) performs a permanent cutting movement at a respectively constant speed and amplitude of the specimen holding device (12) and thus a corresponding continuous cutting function, and the first operating element (28), in its push button function, controls starting and stopping and, in its rotary switch function, the speed of the linearly oscillating cutting movement of the specimen holding device (12) by way of the first drive device (18).

2. A microtome as set forth in claim 1, wherein the speed of the cutting movement of the specimen holding device (12) corresponds to the rotary speed of the first operating element (28) in its standard mode.

3. A microtome as set forth in claim 1 or claim 2, wherein the specimen holding device (12) is provided for performing a linearly oscillating cutting movement.

4. A microtome as set forth in claim 3, wherein the amplitude of the oscillating cutting movement of the specimen holding device (12) corresponds to the amplitude of the rotary movement of the first operating element (28) in its standard mode.

5. A microtome as set forth in claim 4, wherein, when in its second mode, the first operating element (28) is suitable for activation of a motor brake (34) of the first drive device (18).

6. A microtome as set forth in claim 1, wherein the first drive device is a DC motor.

* * * * *